United States Patent [19]

Kutsusawa et al.

[11] 4,383,041
[45] May 10, 1983

[54] AUTOMATIC ENZYME IMMUNOASSAY APPARATUS

[75] Inventors: Tadashi Kutsusawa, Koganei; Hideo Shirane, Tokyo; Mikiharu Fujihara; Hideho Hisada, both of Hachioji, all of Japan

[73] Assignee: Fujizoki Pharmaceutical Co., Ltd., Tokyo, Japan

[21] Appl. No.: 313,682

[22] Filed: Oct. 21, 1981

[30] Foreign Application Priority Data

Oct. 28, 1980 [JP] Japan ................................ 55-150152

[51] Int. Cl.³ .................... G01N 33/54; G01N 33/58; G01N 35/02; G01N 35/06
[52] U.S. Cl. ........................................ 435/291; 422/63; 422/65; 435/288; 436/808
[58] Field of Search .................... 422/63, 65; 435/288; 436/808

[56] References Cited

U.S. PATENT DOCUMENTS

| | | | |
|---|---|---|---|
| 3,932,141 | 1/1976 | Beall | 422/102 |
| 4,087,248 | 5/1978 | Miles | 422/63 |
| 4,224,278 | 9/1980 | Esch | 422/65 |
| 4,265,855 | 5/1981 | Mandle | 422/63 X |
| 4,314,968 | 2/1982 | Guigan | 422/72 X |
| 4,320,087 | 3/1982 | Chau | 422/102 |

Primary Examiner—Sidney Marantz
Attorney, Agent, or Firm—Burgess, Ryan and Wayne

[57] ABSTRACT

An apparatus for automatically performing a sandwich-type enzyme immunoassay. The apparatus includes a rack for holding test tubes. In the test tubes are beads which provide surfaces for the immuochemical reactions. The rack can be moved in lengthwise and transverse directions. Nozzles for supplying and withdrawing liquids from the test tubes are included. The bead in one tube can be transferred to a second tube. The absorbance of a final liquid is measured spectrophotometrically, and the results are recorded by a printer.

1 Claim, 2 Drawing Figures

AUTOMATIC ENZYME IMMUNOASSAY APPARATUS

BACKGROUND OF THE INVENTION

The present invention relates to an automatic enzyme immonoassay apparatus capable of performing enzyme immunoassay automatically, and more particularly to an apparatus for measuring the amount of antigens, haptens or antibodies present in serum.

Enzyme immunoassay is an assay for measuring the amount of an antigen, a hapten or an antibody contained in serum, utilizing an antigen-antibody reaction with the aid of an enzyme. For a more specific explanation of enzyme immunoassay, an example of enzyme immunoassay, the so-called sandwich method, will now be explained.

In the sandwich method, a predetermined amount of an antibody is caused to be deposited on a carrier, for instance, on the surface of a plastic bead, and is made insoluble by converting the antibody to a solid phase fixed to the surface of the carrier.

To the antibody bearing bead is added a predetermined amount of a test solution containing an antigen, the amount of which is to be measured (hereinafter referred to as the test antigen). The antigen is combined with the solidified antibody by the antigen-antibody reaction. The test solution is then removed and the bead is cleaned. A predetermined amount of a reaction solution containing a predetermined amount of an enzyme-labelled antibody, for example, a peroxidase-labelled antibody, is added to the bead. Again an antigen-antibody reaction takes place between the enzyme-labelled antibody and the antigen which has been combined with the antibody solidified and deposited on the bead. The enzyme-labelled antibody which has not combined with the antigen is eliminated, and the activity of the enzyme-labelled antibody which has combined with the antigen is measured, whereby the amount of the test antigen is measured.

In this case, when measuring the activity of peroxidase of the enzyme-labelled antibody which has combined with the solidified antigen, hydrogen peroxide and 2,2'-azinobis (3-ethylbenzothiazoline-6-sulfonic acid) are, for example, employed as a substrate for the enzyme. The bead is washed and unreacted excess peroxidase-labelled antibody is eliminated from the bead. The bead is then immersed in the enzyme substrate solution, and the enzyme substrate solution is colored by the enzyme. The absorbance of the enzyme substrate solution is determined at 405 nm by a spectrophotometer.

In the meantime, reference solutions each containing a known amount of the antigen are prepared and the absorbance of each reference solution is measured, following the steps described above. Thus, a calibration curve is obtained by plotting the amount of the antigen contained in each solution and the absorbance thereof. This calibration curve shows the relationship between the concentration of the antigen in each solution and the absorbance of the solution. By use of that calibration curve, the amount of the antigen contained in the test solution can be determined.

Conventionally, each step in the enzyme immunoassay is conducted manually and, therefore, it takes much time and the results obtained by the manual enzyme immunoassay are not always accurate.

SUMMARY OF THE INVENTION

It is therefore an object of the present invention to provide an automatic enzyme immunoassay apparatus capable of performing enzyme immunoassay automatically.

According to the present invention, enzyme immunoassay, which is conventionally conducted manually, can be automatically conducted accurately and speedily.

DETAILED DESCRIPTION OF THE PREFERRED EMBODIMENT

Figure 1:
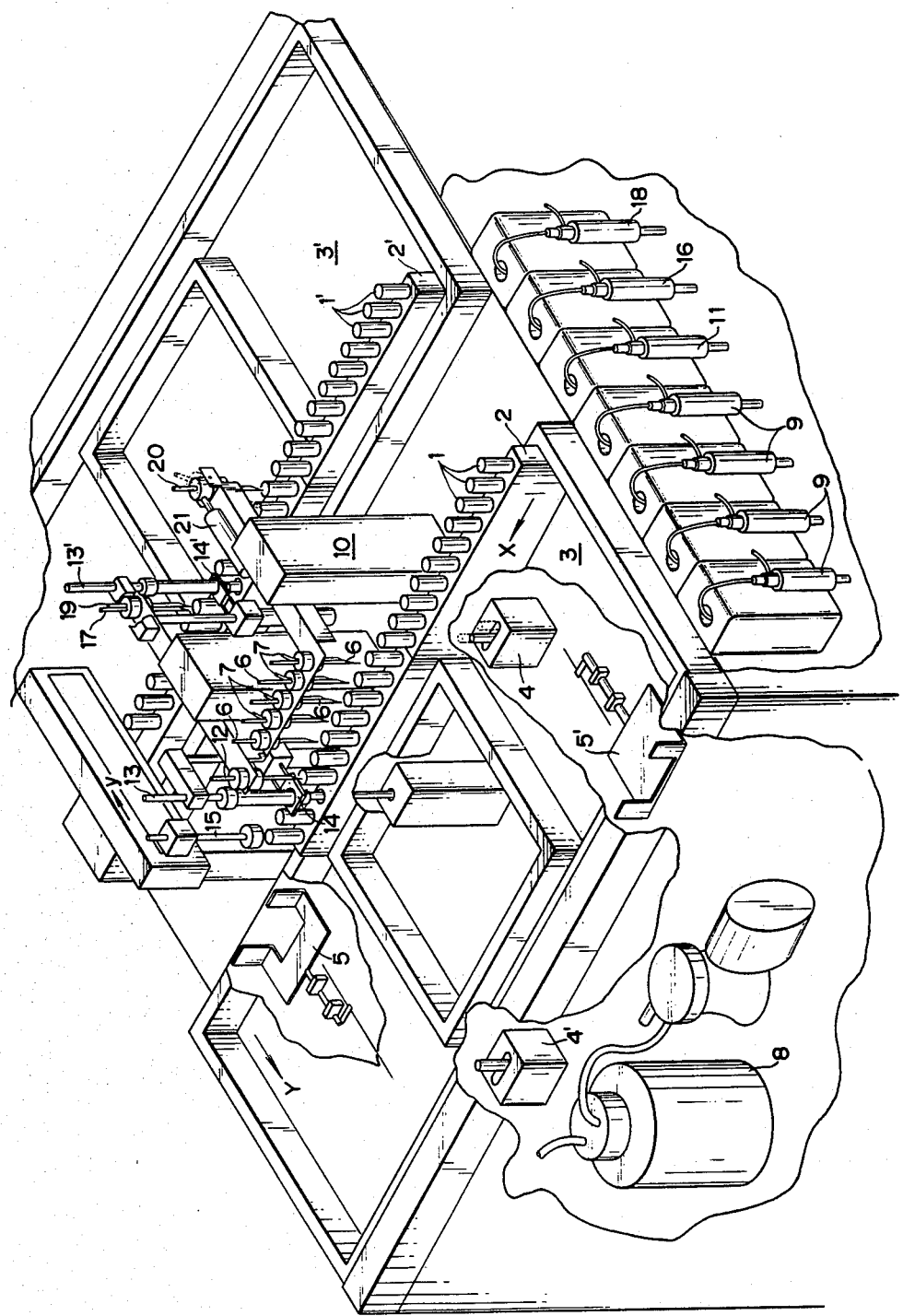
FIG. 1 is a perspective view of the main portion of an embodiment of an automatic enzyme immunoassay apparatus according to the present invention.
Figure 2:
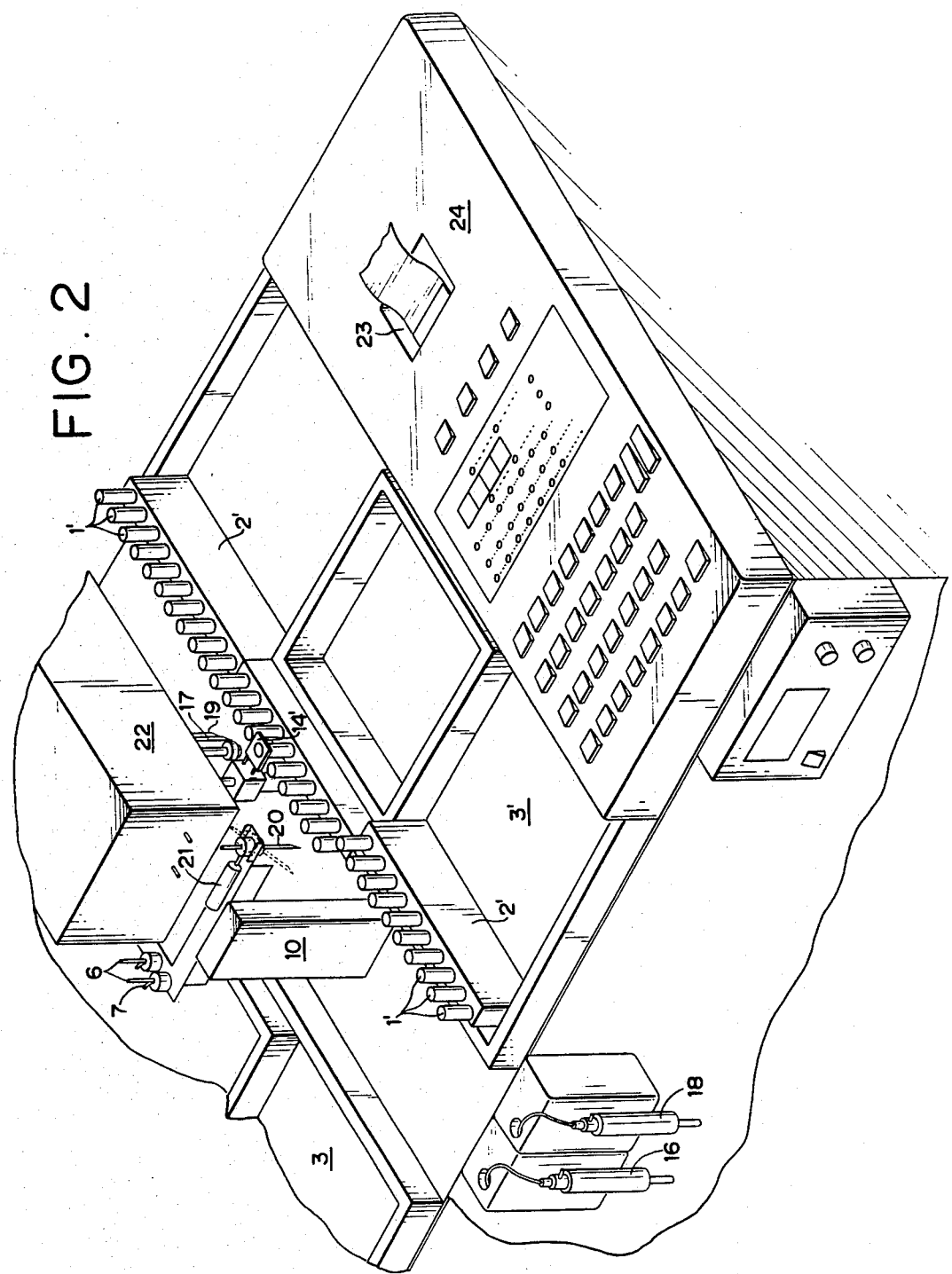
FIG. 2 is another perspective view of the main portion of the automatic enzyme immunoassay apparatus shown in FIG. 1.

Referring to FIG. 1 and FIG. 2, there is shown an embodiment of an automatic enzyme immunoassay apparatus according to the present invention.

As shown in those figures, test tubes 1 and 1' are respectively placed in racks 2 and 2', ten test tubes in each rack. The racks 2 and 2' are respectively incorporated in cages 3 and 3', 22 racks in each cage. The test tubes 1 and 1' each serve as an antigen-antibody reaction chamber.

In each of the test tubes 1, there is placed a plastic bead (not shown) which bears a predetermined amount of a solidified antibody and a predetermined amount of a test liquid (not shown) containing an antigen to be measured, so that an antigen-antibody reaction can take place in each test tube.

The cages 3 and 3' are detachable from the automatic enzyme immunoassay apparatus.

There are disposed driving mechanisms 4 and 4' for driving the racks 2 along the cages 3 lengthwise in the direction of X, and driving mechanisms 5 and 5' for driving the racks 2 transversely in the direction of Y, whereby the test tubes 1 in the rack 2 can be individually moved.

When one of the test tubes 1 comes to a predetermined position and is stopped there, a suction nozzle 6 and a cleaning liquid injection nozzle 7 are inserted into that test tube 1. Upon completion of the antigen-antibody reaction in the test tube 1, the test solution is discarded to a discard bottle 8 through the suction nozzle 6. By the operation of an injector 9, cleaning liquid is injected into the test tube 1 through the cleaning liquid injection nozzle 7, so that the bead (not shown) in the test tube 1 is washed. The cleaning liquid is then evacuated into the suction nozzle 6 and discarded to the discard bottle 8.

The vertical movement of the suction nozzle 6 and the cleaning liquid injection nozzle 7 are performed by an elevator mechanism 10.

After the test tube 1 is moved, a reaction liquid is injected into the test tube 1 through a reaction liquid injection nozzle 12 by a reaction liquid injector 11. The test tube 1 is supported by a support mechanism 13, and vibrations are applied to the test tube 1 by a vibration member 14, so that the bead in the test tube 1 is brought into good "stirring" contact with the reaction liquid. An attraction nozzle 15 is then inserted into the test tube 1 to move the bead upwards by the suction of the attraction nozzle 15. The bead is moved in the direction of Y, while being attracted to the attraction nozzle 15, and is then caused to fall into one of the test tubes 1' placed in the rack 2'.

A substrate is injected into the test tube 1' by a substrate injector 16 and a substrate injection nozzle 17, and the bead is allowed to react with the substrate. A reaction termination liquid is then injected into the test tube 1' by a reaction termination liquid injector 18 and a reaction termination liquid injection nozzle 19. Vibrations are then applied to the test tube 1' by a vibration member 14', so that the contents in the test tube 1' are mixed well.

A measurement nozzle 20 is inserted into the test tube 1' by an air cylinder 21, so that the liquid in the test tube 1' is transported to a measurement apparatus 22, in which the absorbance of the liquid is measured by a spectrophotometer incorporated in the measurement apparatus 22. The measured value is recorded by a printer 23. All of the above-described operations are performed by a microcomputer 24.

According to the present invention, the amount of the antigen contained in the test solution can be detected automatically and the detected result can also be recorded automatically in accordance with the above-described steps.

Preferred examples of a movement apparatus for the rack 2, a vibration mechanism for vibrating the vibration members 14 and 14', and an operation mechanism for operating the attraction nozzle 15 and the measurement nozzle 20 for use in the automatic enzyme immunoassay apparatus will now be explained.

The rack 2 is incorporated in the cage 3. A plurality of pulleys is disposed along the four sides of the cage. A string is trained over those pulleys and the string is rotated by a motor. A drive portion for moving the rack is fixed to the string. A movable lever mechanism is disposed in the drive portion. The top portion of the movable lever is inserted into a hole formed in the bottom of the rack 2, whereby the lever of the movable lever mechanism is moved as the string is rotated and the rack 2 is also moved.

The vibration members 14 and 14' are connected to a permanent magnet (for instance, a magnet made of barium ferrite) through an intermediate plate. The permanent magnet is caused to vibrate by an A.C. magnetic field generation apparatus which is disposed near the permanent magnet. The vibrations generated are transmitted to the test tube through the intermediate plate and the vibration members, so that the contents in the test tube are mixed.

The attraction nozzle 15 is inserted into the test tube in which a bead is placed. The top end of the attraction nozzle 15 is brought into contact with the bead. With the reduction in pressure in the nozzle, the bead is attracted to the top end of the nozzle and is then removed from the test tube. The nozzle, with the bead attracted to the top end thereof, is inserted into another test tube and the pressure in the nozzle is returned to atmospheric pressure, so that the bead is caused to fall into the test tube.

It is preferable that the measurement nozzle 20 be held inclined with respect to the test tube after it has been pulled from the test tube, in order to prevent other liquids from attaching themselves to the measurement nozzle 20. In order to do this, a holder of the nozzle 20 is attached to the piston of the air cylinder, so that the holder is rotated by the linear movement of the piston, whereby the nozzle is held vertically or with an inclination (about 45 degrees) with respect to the test tube.

What is claimed is:

1. An automatic enzyme immunoassay apparatus comprising:

means for moving a rack holding test tubes containing beads therein, in a lengthwise direction, said rack being held in a cage;

means for moving said rack in a direction transverse to said lengthwise direction;

means for inserting both a suction nozzle and a cleaning liquid injection nozzle into any of or into a plurality of said test tubes to inject cleaning liquid into said test tube after withdrawing liquid by suction from said test tube and discarding the withdrawn liquid;

means for inserting a reaction liquid injection nozzle into said test tube and injecting a reaction liquid into said test tube;

means for vibrating said test tube;

means for inserting an attraction nozzle into said test tube and pulling said bead out of said test tube, while attracting said bead thereto, and letting said bead fall into a second test tube;

means for inserting a substrate injection nozzle and a reaction termination liquid injection nozzle, and injecting a reaction termination liquid into said second test tube after injecting a substrate;

means for inserting a nozzle associated with a measuring device into said second test tube and transporting the liquid in said test tube to a measurement device;

a spectrophotometer for measuring the absorbance of said liquid; and a printer for recording the measured value of the absorbance.

* * * * *